(12) United States Patent
Hedington et al.

(10) Patent No.: US 6,868,987 B2
(45) Date of Patent: Mar. 22, 2005

(54) FLUID BAGS WITH AN INTEGRAL TUBE-LIKE PASSAGEWAY FOR COOPERATION WITH A PERISTALTIC PUMP DEVICE

(75) Inventors: John Graham Hedington, Halstead (GB); Stuart Richard Page, Halstead (GB)

(73) Assignee: Constance Limited (GB)

( * ) Notice: Subject to any disclaimer, the term of this patent is extended or adjusted under 35 U.S.C. 154(b) by 267 days.

(21) Appl. No.: 10/296,514
(22) PCT Filed: May 25, 2001
(86) PCT No.: PCT/GB01/02321
§ 371 (c)(1), (2), (4) Date: Nov. 25, 2002
(87) PCT Pub. No.: WO01/91831
PCT Pub. Date: Dec. 6, 2001

(65) Prior Publication Data
US 2004/0007590 A1 Jan. 15, 2004

(51) Int. Cl.[7] .............................................. A61M 5/142
(52) U.S. Cl. ...................... 222/95; 222/102; 222/105; 222/207; 222/214; 222/383.2; 222/145.5; 222/145.6
(58) Field of Search .......................... 222/95, 102, 105, 222/207, 214, 383.2, 145.5, 145.6

(56) References Cited
U.S. PATENT DOCUMENTS

| | | | | |
|---|---|---|---|---|
| 3,774,762 A | * | 11/1973 | Lichtenstein | 210/94 |
| 4,334,640 A | * | 6/1982 | van Overbruggen et al. | 222/207 |
| 4,513,885 A | * | 4/1985 | Hogan | 222/95 |
| 4,690,307 A | * | 9/1987 | Hogan | 222/95 |
| 4,717,047 A | * | 1/1988 | van Overbruggen et al. | 222/207 |
| 4,921,150 A | * | 5/1990 | Lagergren et al. | 222/214 |
| 5,803,317 A | * | 9/1998 | Wheeler | 222/214 |
| 6,012,611 A | * | 1/2000 | Schroeder | 222/105 |
| 6,016,935 A | * | 1/2000 | Huegerich et al. | 222/214 |
| 6,142,340 A | * | 11/2000 | Watanabe et al. | 222/214 |

FOREIGN PATENT DOCUMENTS

| | | | | |
|---|---|---|---|---|
| DE | 19534502 A1 | * | 3/1997 | A61M/1/00 |
| EP | 615735 A1 | * | 9/1994 | A61F/5/44 |

* cited by examiner

Primary Examiner—Kenneth Bomberg
(74) Attorney, Agent, or Firm—McGarry Bair PC

(57) ABSTRACT

A bag is provided for containing a liquid intended to be supplied in a controlled manner to some other site, for example to a medical patient. The main bag portion has a pair of overlying side walls joined together around their edges, the side walls having integral extensions which together define an outlet region in communication with the interior of the main portion of the bag. The extensions are bonded together to define a tube-like passageway extending throughout the outlet region from the interior of the bag. The extensions are adapted to permit the connection thereto of a peristaltic pump device co-operable with the tube-like passageway to control the out-flow of liquid from the bag.

14 Claims, 4 Drawing Sheets

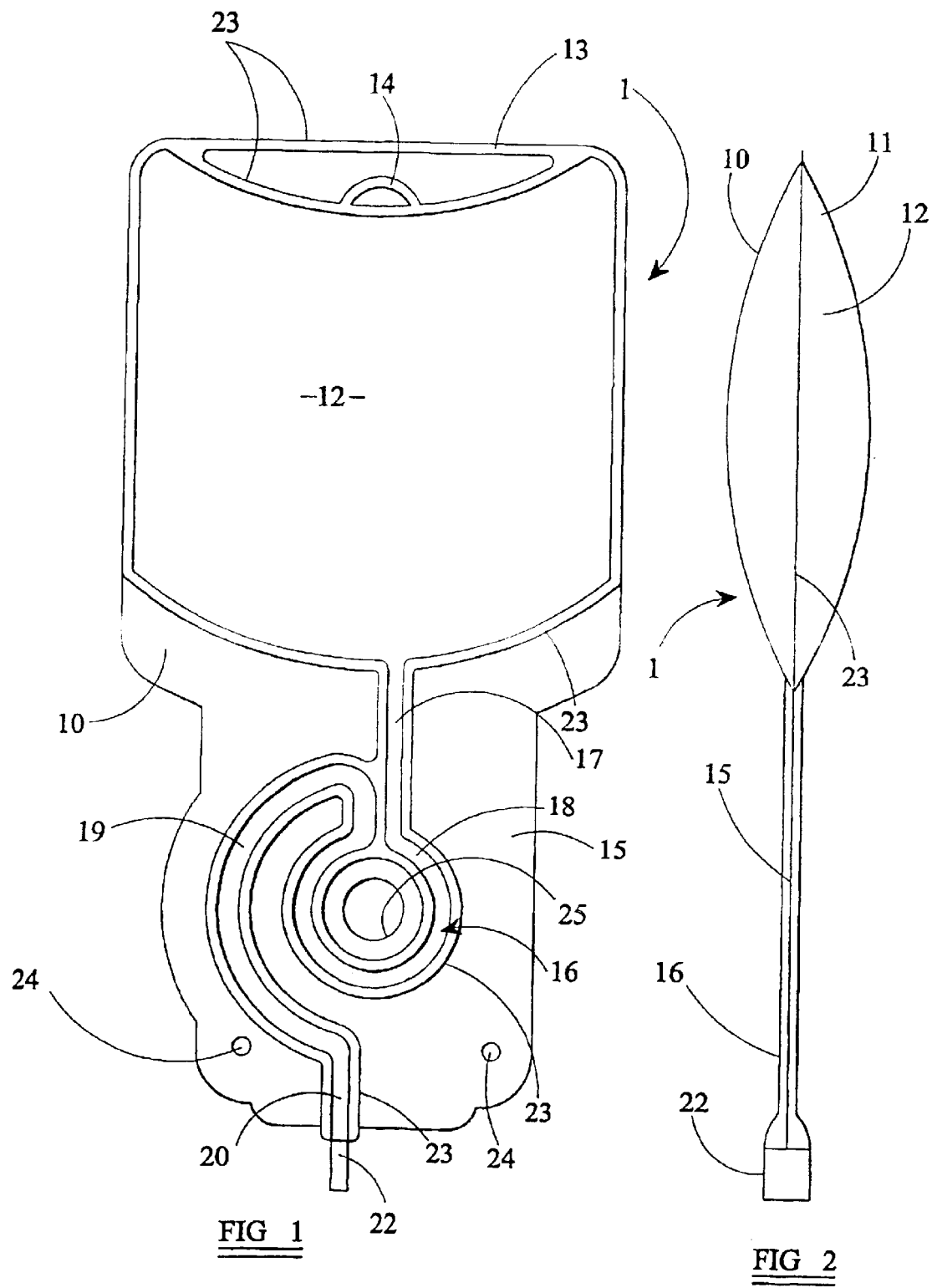

FIG_4

FLUID BAGS WITH AN INTEGRAL TUBE-LIKE PASSAGEWAY FOR COOPERATION WITH A PERISTALTIC PUMP DEVICE

CROSS-REFERENCE TO RELATED APPLICATIONS

This application claims priority on International Application No. PCT/GB01/02321, filed May 25, 2001, which claims priority on British Application No. 0012931.2, filed May 26, 2000.

This invention relates to a bag for containing a liquid, and in particular to a bag which is adapted for use in circumstances where a gradual outflow of the contained liquid is required.

Though the invention is primarily concerned with a bag for containing a sterile liquid for use in the medical industry, as a source of liquid for supply to a human body by way of an intravenous catheter, it will be appreciated that the invention is not to be regarded as limited to that use and may find application in other industries. Nevertheless, the invention will be described hereinafter solely with reference to its use for healthcare.

In all branches of healthcare, bags for the supply of liquids to the human (or even animal) body are widely used, by means of intravenous introduction. Mostly those liquids are supplied by suspending the bag above the body and allowing the liquid to run through a restriction to an intravenous catheter inserted into the patient's body. The restriction usually is adjustable, to permit the required flow rate to be set by observing the rate at which drops of the liquid fall through the restriction into a chamber immediately therebelow. Unfortunately, it is not possible to achieve accurate flow rates which can be maintained for a relatively long period of time. In particular, also temperature effects can affect the liquid viscosity and the flow rate through the restriction. Moreover, if a rate of flow higher than an observable drip rate is required, some other technique must be employed for determining the actual flow rate.

In order to overcome the above disadvantages, it is known to position a liquid bag within a bag squeezer having a piston which is power driven at a controlled rate, so as to drive liquid from the bag. Though such squeezers are known in the healthcare industry, in general they are not widely used since they tend to be unreliable in operation, and complete emptying of a bag is very difficult with such equipment.

If a flow rate higher than that which con be achieved with a drip is required, with good accuracy, it is known to employ a peristaltic pump having a flexible tube which is arranged in the pipe from the bag to the catheter. The operation of the pump may be closely controlled in order to achieve a desired flow rate through the tube, conducting liquid from the bag to the patient's body. After use, the cleaning of the pump tube is time consuming, or in the alternative, if the tube is scrapped, significant costs are involved, since the pump requires a tube of known, controlled characteristics. Further, it is necessary to have multiple junctions in the pipe from the bag to the catheter, leading to the possibility of disconnection should the patient move, leaks, and maybe even allowing the introduction of bacteria into the pipe.

The present invention aims at addressing the above issues and allowing the use of a peristaltic pump in association with a bag containing a liquid intended to be supplied over a period of time to a patient, at a known and controlled flow rate.

Accordingly, one aspect of this invention provides bag for containing a liquid intended to be supplied in a controlled manner to some other site, comprising a main bag portion having a pair of overlying side walls joined together around their edges thereby to define a reservoir for the liquid, the side walls having a pair of integral overlying extensions projecting from the conjoined edges so as to form a pump area projecting from one side of the bag, the extensions being bonded together to define a tube-like passageway having a section of part circular form and extending from the interior of the reservoir for fluid to an outlet region at an edge of the pump area, the extensions being profiled and adapted to permit the connection thereto of a peristaltic pump device having pump members driven around a circular path centered on the centre of said section of the passageway, whereby the connection of the peristaltic pump device to the extensions and co-operable with the passageway controls the out-flow of liquid from the reservoir.

The major part of the bag of the present invention may be essentially the same as the bags already widely in use throughout the healthcare industry, for containing liquids to be supplied intravenously to patients. However, at the lower end of such a bag (considering the bag when suspended for the supply of liquid) the two side walls defining the bag have integral overlying extensions which are profiled and adapted to permit the direct connection thereto of a peristaltic pump device co-operating with the tube-like passageway formed by the walls of the bag extension. During manufacture of the bag, the sheets which form the side walls and the extensions may be given the required flexibility properties for co-operation with the peristaltic pump, so obviating the need for the use of a special tube intended expressly for use with a peristaltic pump.

The passageway is formed by bonding together the two overlying extensions in such a way that the passageway extends across those extensions, from the main portion of the bag to an edge of the extensions where a conventional intravenous supply pipe may be connected to the passageway. For this purpose, a connector socket or spigot may be provided as a part of the bag, which socket or spigot may connect directly to an intravenous supply pipe leading to a catheter. The bonding together of the overlying extensions and also the provision of a socket or spigot, to form the tube-like passageway therebetween, may be performed by use of heat sealing, sonic sealing or RF sealing techniques.

The passageway has a part-circular form, so as to be suitable for use with a rotary peristaltic pump having pumping members engaged with the passageway and running in a circular path overlying the part-circular form of the passageway, to drive fluid therealong.

In a particularly preferred form of bag of this invention, the bag has extensions which define a passageway having a linear first portion leading from the bottom of the bag (considering the normal disposition of the bag when suspended for use) into the extensions, a part-circular second portion of constant radius and extending for some 300° to 340° of arc, a part-circular third portion doubled back to extend around part of the second portion, and a linear fourth portion leading from the end of the third portion to an common edge of the extensions. In a modification of this, the order of the second and third portions is reversed.

The overall shape of the extensions may have any required shape to permit the connection thereto of a peristaltic pump, having regard to the design of the pump itself. Typically, there will be flanges to both sides of the passageway, together with apertures through the flanges, for registration purposes with corresponding projections provided on the pump. Such a pump may have a base plate including such projections and on which the extensions of the bag are placed, and an actuator carrying the peristaltic pumping members together with a drive arrangement therefor which actuator may be attached to the base plate so clamping the bag extensions therebetween. This invention extends to a bag for the supply of liquid as described hereinbefore together with a peristaltic pump, the extensions of the bag being configured for co-operation with the pump whereby liquid from the bag may be pumped at a controlled rate from the bag to some other site.

By way of example only, some specific embodiments of liquid supply bag arranged in accordance with the present invention will now be described, reference being made to the accompanying drawings, in which:

FIG. 1 is a plan view of a first embodiment of bag;

FIG. 2 is an edge view on the bag of FIG. 1;

Figure 3:
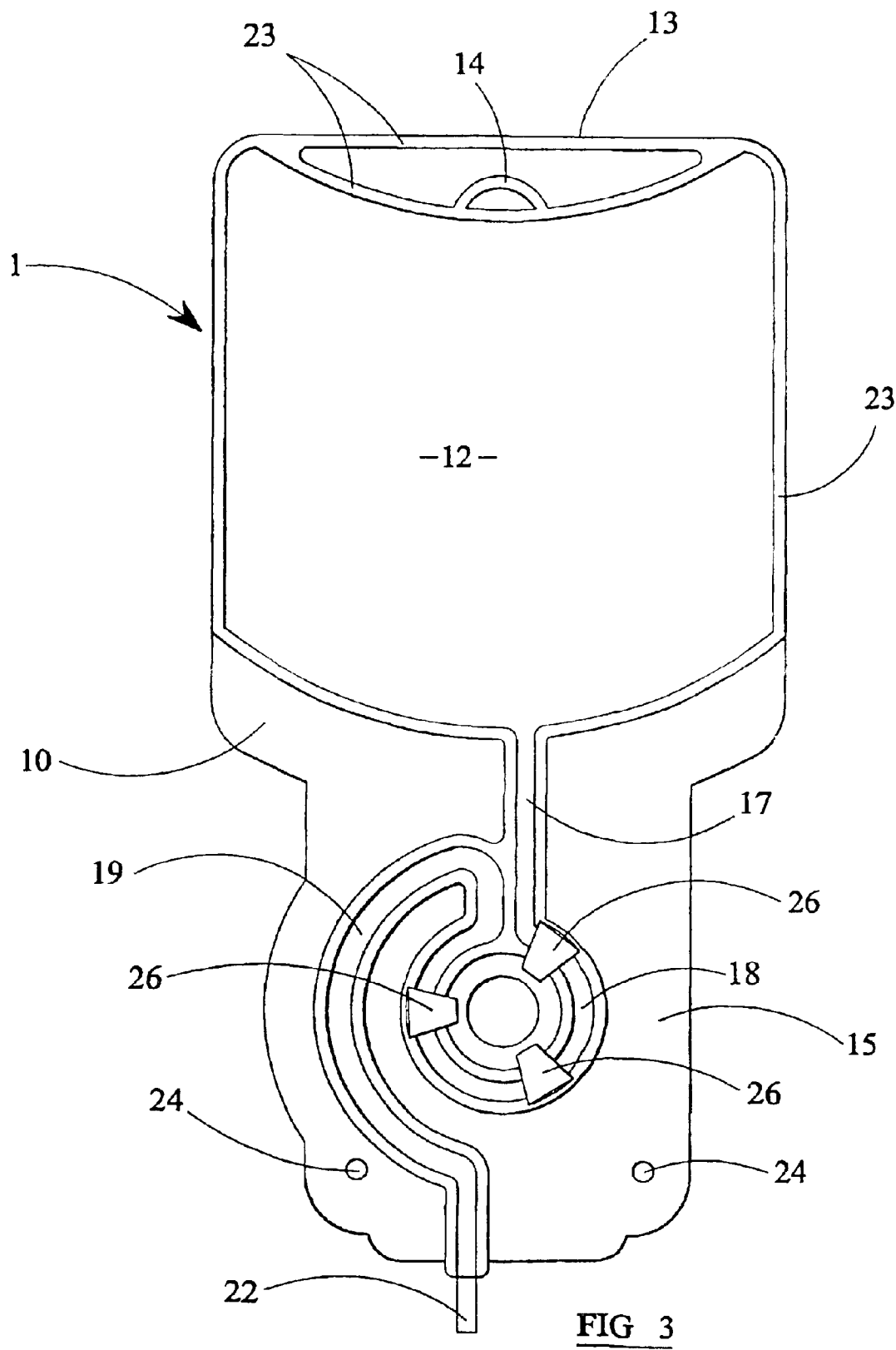
FIG. 3 illustrates peristaltic pump members engaged with the tube of the extensions of the bag of FIGS. 1 and 2.

FIGS. 1 and 2 show the first embodiment of bag in its normal orientation, when the bag is to be used for the supply of a contained liquid to a patient. The bag 1 comprises two sheets of medically stable plastics material 10, 11, each of the same shape and with their edges bonded together so as to define a main portion 12 within which liquid is contained before its supply to a patient. At the upper end of the bag there is a carrying handle 13 formed integrally with the bag and a suspension hanger 14 by means of which the bag may be positioned on a hook provided on a stand or frame, in a manner known in the art, for arrangement adjacent a patient. Thus, the bag may be disposed above a patient, as is conventional with gravity feed, or on the same level or even below a patient, since the liquid is to be pumped from the bag, at a constant head.

Below the main portion 12 of the bag, each of the side sheets 10, 11 has a generally rectangular extension 15. Between those extensions 15 there is defined a passageway 16, by suitably bonding together the two extensions. Preferably, one of the extensions is flat, even where the passageway 16 is present, and the other sheet, as considered in cross-section, is convexly curved in the region of the passageway though flat elsewhere. In this way the passageway formed has a D-shaped cross-section. As shown, that passageway has a generally linear first portion 17 leading from the bottom of the main portion of the bag and opening into a part-circular second portion 18 of constant radius and extending for a little less than 360°, say 300° to 340°, so as to have a C-shape. The circular second portion 18 then leads into a further part-circular third portion 19, extending around the outside of one-half of the circular second portion 18 in the opposite direction thereto. That third portion 19 leads into a linear fourth portion 20 running to lower edge 21 of the extensions, remote from the main area of the bag. A pipe connecting spigot 22 is secured to the end of the fourth portion 20 of the passageway 16, to permit the connection thereto of a conventional intravenous catheter flexible pipe.

As shown in the drawings, the principal areas of the bag and of the passageway are defined by strong bonds 23 between the sheets 10 and 11, which may be formed for example by thermal welding, sonic welding or RF welding. The regions of extensions 15 outside the lines of these welds are joined together for example by means of a simple adhesive or by a simpler welding process performed to a lower standard than the strong bonds 23.

The extensions 15 themselves are profiled having regard to the design of a peristaltic pump with which the bag is intended to be used. In FIGS. 1 and 3 the extensions 15 are shown as being of lesser width than the main portion 12. It is to be understood, however, that they could be of the same width as the main portion 12 or a greater width than the main portion 12. Further, those extensions include a pair of registration holes 24, which may locate on pegs provided on the pump, to give proper alignment between the circular second portion 18 of the passageway 16 and the pumping members of the peristaltic pump. In addition, there is a central hole 25 through the extensions 15 concentric with the circular second portion 18, for location on the operating part of a peristaltic pump.

Though the walls defining the main area of the bag are integral with those of the extensions 15, nevertheless the plastics sheets from which those walls are made may be modified in order to allow the tube 16 formed within the extensions to have the required properties for pumping by means of an attached peristaltic pump. For example, the extensions 15 may have a thinner wall thickness to give greater flexibility to the passageway 16, to facilitate pumping. In the alternative, those extensions may have a greater wall thickness, in order to accommodate the on-going flexing of the passageway 16 caused by operation of an attached peristaltic pump. That greater wall thickness may be achieved by laminating a second sheet with the sheet defining the main area of the bag together with the integral extension, that second sheet being laminated only over the area of the integral extension 15.

An advantage of having the passageway 16 defined by walls of a greater thickness is that the passageway may be given a measure of resilience, to return the passageway to its original shape before compression by the pump members. This recovery of the passageway shape would encourage the drawing of fluid into the passageway from the bag, so reducing the dependence on gravity feeding.

The extensions 15 may carry a label identifying the content of the associated bag. Such a label may include a bar-code or a programmable device which may then be read by a reader associated with the pump. The read information may be displayed by a control circuit associated with the pump, and such a control circuit could even prevent the administration of excessive doses, from information read from the label.

FIG. 3 shows the positioning of the extension 15 with respect to the rotary pumping elements 26 of a peristaltic pump. The elements are mounted to roll continuously around the circular second portion 18 of the passageway 16, in contact with the convexly curved surface of the passageway, thereby effecting positive displacement pumping of liquid out of the bag and along the passageway 16 to the outlet spigot 22. The pump includes a power drive arrangement (not shown) for the pumping elements 26, adjustable to give the required liquid flow-rate through the passageway 16 and into a pipe (not shown) connected to the spigot 22. That flow-rate may be calculated by using the cross-sectional area of the passageway 16 in the region of the circular second portion 18, together with the rotational speed of the pump.

An advantage of a pump arrangement as shown is that fluid cannot free-flow through the passageway 16 from the bag. There will always be one rolling pumping element 26 closing off the passageway and driving liquid in front of the roller, when the pump is being driven. Equally, if the pump is stopped, liquid cannot flow from a patient back to the bag.

In addition, however, the passageway 16 may be provided at the downstream end with a self-sealing closure, openable by the peristaltic pump when the bag is in position in the pump.

A peristaltic pump may be made relatively simply and be of light weight so that it may be clamped to the extensions 15 and suspended with the bag from the hanger 14. The pump may include a self-contained power supply for the pumping elements, or may be supplied with electricity from a remote power pack. One example of a suitable pump is described in our International patent application filed on even date herewith under the title "Peristaltic Pumps", claiming priority from UK patent application No. 0012930.4 which is incorporated herein by reference.

Figure 4:
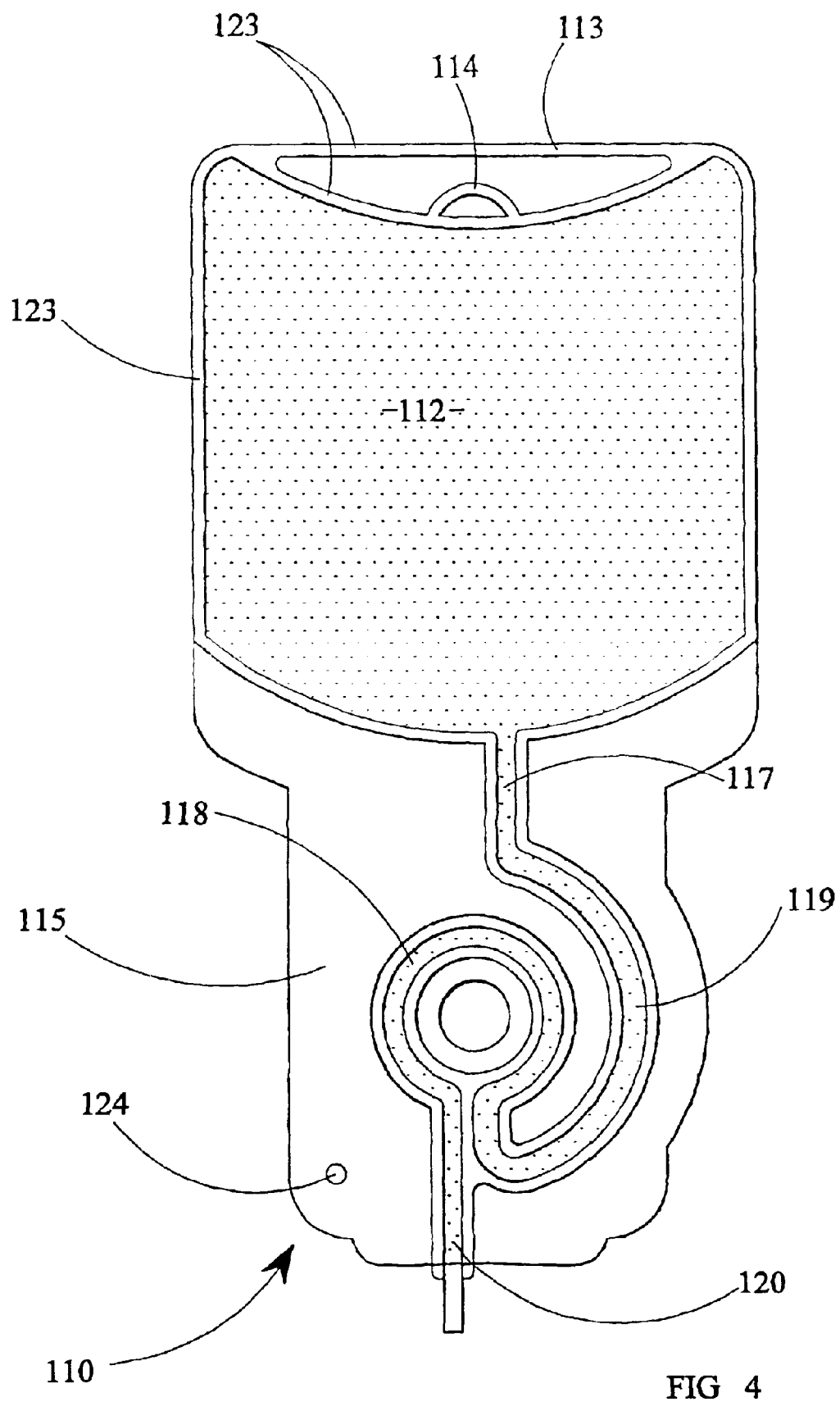
FIG. 4 is a plan view of a second embodiment of bag.

A number of modifications may be made in the bag shown in FIGS. 1 to 3. One of these is shown in FIG. 4, where the bag is denoted as 101. Elements in FIG. 4 which correspond in substance to elements in FIGS. 1 to 3 are given the same numerals, but with the addition of 100. As will be seen, the bag 101 differs from the bag 1 in that the portions of the passageway 116 are arranged in a different order to those of passageway 16. Thus, the passageway 116 is formed successively of a generally linear portion 117, a part-circular portion 119, a circular portion 118 (for engagement with the pumping elements) of constant radius and extending for a little less than 360°, say 300° to 340°, and a linear fourth position 120. This may have an advantage over the passageway 16, in that it reduces the length of the portion of the passageway which is downstream of that which is engaged by the pumping elements. This may help reduce undesirable fluctuations in the pressure of the liquid as it is supplied to the patient.

Figure 5:
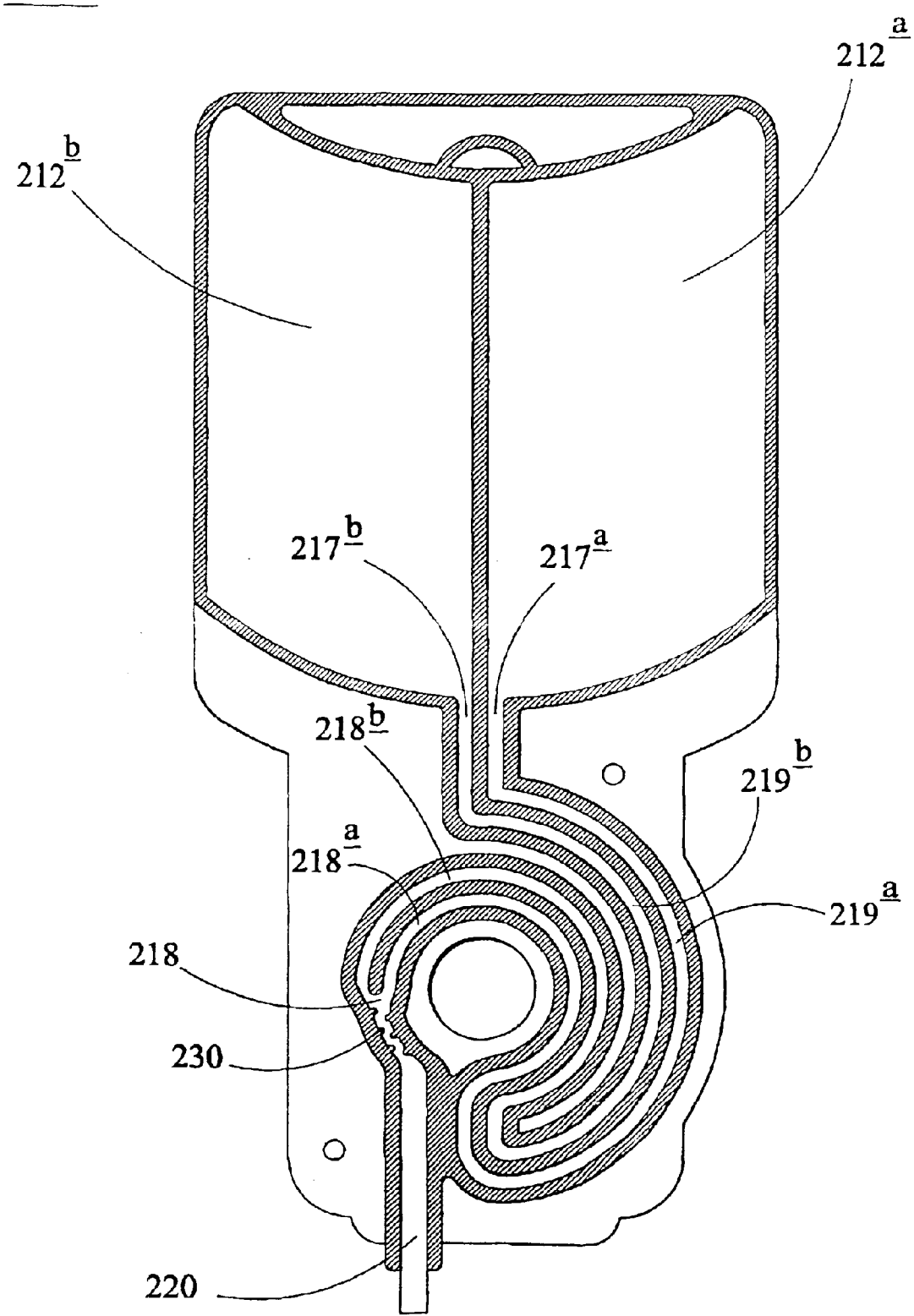
FIG. 5 is a plan view of a third embodiment of bag.

A further modification is shown in FIG. 5, which illustrates a bag 201. Elements in FIG. 5 which correspond in substance to elements in FIGS. 1 to 3 are given the same numerals, but with the addition of 200. The bag of FIG. 5 is distinguished by the fact that it has a plurality of passageways 219 in parallel with one another. FIG. 5 shows two passageways, but it is to be understood that more than two could be provided. The main portion of the bag has two sub-portions 212a and 212b, for separately containing two liquids, each portion 212a, 212b communicating with the upstream end of a respective one of the passageways. The passageways themselves resemble the passageway shown in FIG. 4, and each have separate portions 217a, 217b and 219a and 219b. Their circular portions 218a and 218b are separate at their upstream ends but merge into a common portion 218, where the liquids mix with one another. To assist mixing, the mixing portions 218 may be provided with mixing means, for example in the form of protrusions 230, which induce turbulence in the liquids. Finally, there is a common portion 220 leading to the bag outlet.

The bag shown in FIG. 5 permits the storage and delivery of two liquids which require to be delivered together but which cannot satisfactorily be stored together. The delivery is effected using a single set of pumping elements, which ensures that the two liquids are delivered in whatever may be the desired ratio, as predetermined, for example, by the respective cross-sections of the two passageways. It is to be understood that although FIG. 5 is shown as a modification of the passageway layout of FIG. 4, one could alternatively use a modification of the passageway layout of FIG. 1.

Though a bag intended for containing a liquid for supply to the human body must be made of medical grades of plastics material and must be made under controlled sterile conditions, it will be appreciated that the bag is relatively cheap to manufacture and may be used with a peristaltic pump without any further modification. It is thus simple and easy to use in the healthcare industry and may be regarded as a disposable item, when empty. By contrast the peristaltic pump may be used as often as is required by disconnecting it from an empty bag and reconnecting it to a fresh bag.

We claim:

1. A bag for containing a liquid intended to be supplied in a controlled manner to some other site, comprising a main bag portion having a pair of overlying side walls joined together around their edges thereby to define a reservoir for the liquid, the side walls having a pair of integral overlying extensions projecting from the conjoined edges so as to form a pump area projecting from one side of the bag, the extensions being bonded together to define a tube-like passageway having a section of part circular form and extending from the interior of the reservoir for fluid to an outlet region at an edge of the pump area, the extensions being profiled and adapted to permit the connection thereto of a peristaltic pump device having pump members driven around a circular path centered on the center of said section of the passageway, whereby the connection of the peristaltic pump device to the extensions and co-operable with the passageway controls the out-flow of liquid from the reservoir.

2. A bag as claimed in claim 1, wherein the passageway comprises successively, as considered from its reservoir end to its outlet region, a generally linear first portion, the part-circular second portion, a part-circular third portion extending round the outside of part of the second portion, and a linear fourth portion.

3. A bag as claimed in claim 1, wherein the passageway comprises successively, as considered from its reservoir end to its outlet region, a generally linear first portion, a part-circular second portion, a part-circular third portion, with the second portion extending round the outside of part of the third portion, and a linear fourth portion.

4. A bag as claimed in claim 1, wherein the outlet region of the passageway is provided with a socket or spigot for the direct connection thereto of an intravenous catheter supply pipe.

5. A bag as claimed in claim 4, wherein the socket or spigot is separately formed and is bonded to the extensions to communicate with said passageway.

6. A bag as claimed in claim 1, wherein the extensions include registration openings for mating with corresponding projections provided on a peristaltic pump with which the bag is to be used, to obtain alignment between the passageway in the extensions and pumping members of the pump.

7. A bag as claimed in claim 1, wherein the passageway in the extensions is defined by lines of thermal, sonic or RF welding bonding together the two overlying side walls forming the extensions.

8. A bag as claimed in claim 1, wherein the end of the main bag portion remote from the extensions is provided with an integral suspension hanger.

9. A bag as claimed in claim 1, wherein, as viewed in cross-section, the passageway is defined by a flat portion of one of the extensions and a convexly curved portion of the other of the extensions.

10. A bag as claimed in claim 1, wherein the main bag portion defines a plurality of sub-portions for separately containing a plurality of liquids, and wherein the extensions define a corresponding plurality of passageways each of which communicates at its upstream end with a respective one of the sub-portions.

11. A bag as claimed in claim 10, wherein the plurality of passageways run substantially parallel to one another.

12. A bag as claimed in claim 10, wherein the passageways merge with one another before the outlet region thereof.

13. A bag as claimed in claim 12, comprising mixing means for assisting mixing of the liquids after the passageways have merged.

14. The combination of a bag as claimed in claim 1 and a peristaltic pump, the extensions of the bag being configured for cooperation with the pump whereby liquid may be pumped from the bag at a controlled rate.

* * * * *